US012179588B2

(12) United States Patent
Jung et al.

(10) Patent No.: US 12,179,588 B2
(45) Date of Patent: Dec. 31, 2024

(54) DRUNK DRIVING PREVENTION SYSTEM WITH BYPASS MODE AND DRUNK DRIVING PREVENTION METHOD USING THE SYSTEM

(71) Applicant: HYUNDAI MOBIS CO., LTD., Seoul (KR)

(72) Inventors: Yu Jin Jung, Uiwang-si (KR); Chang Won Lee, Seoul (KR); June Seung Lee, Yongin-si (KR); Yeon Su Kim, Gunpo-si (KR)

(73) Assignee: HYUNDAI MOBIS CO., LTD., Seoul (KR)

( * ) Notice: Subject to any disclaimer, the term of this patent is extended or adjusted under 35 U.S.C. 154(b) by 238 days.

(21) Appl. No.: 17/877,212

(22) Filed: Jul. 29, 2022

(65) Prior Publication Data
US 2023/0040522 A1    Feb. 9, 2023

(30) Foreign Application Priority Data
Aug. 5, 2021  (KR) .................. 10-2021-0103020

(51) Int. Cl.
*B60K 28/06* (2006.01)
*A61B 5/08* (2006.01)
(Continued)

(52) U.S. Cl.
CPC ............ *B60K 28/063* (2013.01); *A61B 5/082* (2013.01); *B60K 28/06* (2013.01); *B60W 50/085* (2013.01);
(Continued)

(58) Field of Classification Search
None
See application file for complete search history.

(56) References Cited

U.S. PATENT DOCUMENTS

| 4,436,176 A | * | 3/1984 | Cota | B60K 28/063 |
| | | | | 180/287 |
| 4,697,666 A | * | 10/1987 | Collier | B60K 28/063 |
| | | | | 340/576 |

(Continued)

FOREIGN PATENT DOCUMENTS

| AU | 2003286799 A1 | * | 6/2005 | ........... B60K 28/063 |
| AU | 2007215469 A1 | * | 8/2008 | ............. A61B 5/145 |

(Continued)

OTHER PUBLICATIONS

Extended European Search Report issued on Dec. 23, 2022 in corresponding European patent application No. 22186875.5.

*Primary Examiner* — Kevin R Steckbauer
(74) *Attorney, Agent, or Firm* — NovoTechIP International PLLC (57) ABSTRACT

Disclosed are a drunk driving prevention system and a drunk driving prevention method using the system that includes a sensor module measuring the alcohol content in exhaled breath of a driver at the time of breath-checking of the driver and a control module configured to check an intoxication state of the driver based on the alcohol content measured by the sensor module to determine whether or not a breath-checking is complete and block an engine start when the breath-checking fails, wherein the control module includes a bypass control unit switching a vehicle into a drivable state when the breath-checking fails.

12 Claims, 3 Drawing Sheets

(51) Int. Cl.
    *B60W 50/08*         (2020.01)
    *B60W 50/14*         (2020.01)
    *B60W 40/08*         (2012.01)
    *B60W 50/12*         (2012.01)

(52) U.S. Cl.
    CPC ......... *B60W 50/14* (2013.01); *A61B 2503/22* (2013.01); *B60K 28/066* (2013.01); *B60W 2040/0836* (2013.01); *B60W 50/12* (2013.01); *B60W 2050/146* (2013.01); *B60W 2420/403* (2013.01); *B60W 2510/1005* (2013.01); *B60W 2520/10* (2013.01); *B60W 2540/24* (2013.01); *B60W 2556/45* (2020.02)

(56) References Cited

U.S. PATENT DOCUMENTS

| | | | | |
|---|---|---|---|---|
| 4,723,625 | A * | 2/1988 | Komlos | B60K 28/063 340/576 |
| 5,020,628 | A * | 6/1991 | Bigliardi | G01N 33/4972 340/576 |
| 5,743,349 | A * | 4/1998 | Steinberg | B60K 28/063 180/272 |
| 7,204,335 | B2 * | 4/2007 | Stewart | B60K 28/063 340/576 |
| 7,227,472 | B1 * | 6/2007 | Roe | B60K 28/06 340/576 |
| 7,394,392 | B1 * | 7/2008 | Roe | B60K 28/06 340/576 |
| 7,451,852 | B2 * | 11/2008 | Stewart | B60K 28/063 340/576 |
| 7,667,609 | B1 * | 2/2010 | Roe | B60K 28/06 340/576 |
| 8,469,135 | B2 * | 6/2013 | Kaschner | B60K 28/063 701/1 |
| 9,884,628 | B1 * | 2/2018 | Grant | B60W 40/08 |
| 10,227,063 | B2 * | 3/2019 | Abreu | B60T 7/14 |
| 10,525,979 | B1 * | 1/2020 | Grant | B60W 40/08 |
| 2002/0084130 | A1 * | 7/2002 | Der Ghazarian | B60K 28/063 180/272 |
| 2004/0138823 | A1 * | 7/2004 | Gollar | G01N 33/4972 702/19 |
| 2005/0241871 | A1 * | 11/2005 | Stewart | B60K 28/063 180/272 |
| 2007/0144812 | A1 * | 6/2007 | Stewart | B60K 28/063 307/10.6 |
| 2009/0043409 | A1 * | 2/2009 | Ota | B60K 28/063 340/576 |
| 2010/0274411 | A1 * | 10/2010 | Ozaki | B60K 28/063 701/1 |
| 2010/0312431 | A1 * | 12/2010 | Kaschner | B60K 28/063 701/1 |
| 2012/0073892 | A1 * | 3/2012 | Hunter | B60K 28/063 180/273 |
| 2015/0094914 | A1 * | 4/2015 | Abreu | B60H 1/00742 701/1 |
| 2018/0339706 | A1 * | 11/2018 | Biondo | B60W 50/10 |
| 2020/0171944 | A1 * | 6/2020 | Hanna | B60W 50/0098 |
| 2023/0040522 | A1 * | 2/2023 | Jung | A61B 5/082 |

FOREIGN PATENT DOCUMENTS

| | | | | |
|---|---|---|---|---|
| AU | 2008311107 A1 * | 3/2010 | | A61B 5/082 |
| AU | 2008311107 B2 * | 11/2011 | | A61B 5/082 |
| AU | 2011307196 A1 * | 4/2013 | | A61B 10/0045 |
| CA | 2641694 A1 * | 8/2007 | | A61B 5/145 |
| CA | 2539073 C * | 1/2009 | | B60K 28/063 |
| CA | 2816399 A1 * | 3/2012 | | B60K 28/063 |
| CN | 115703351 A * | 2/2023 | | A61B 5/082 |
| DE | 102007047709 A1 * | 4/2009 | | B60K 28/063 |
| EP | 2197701 B1 * | 1/2014 | | B60K 28/063 |
| EP | 2733463 A1 * | 5/2014 | | B60K 28/063 |
| EP | 1678001 B1 * | 11/2018 | | B60K 28/063 |
| EP | 4129735 A1 * | 2/2023 | | A61B 5/082 |
| JP | 2005096663 A | 4/2005 | | |
| JP | 5348457 B2 | 11/2013 | | |
| KR | 101705968 B1 | 2/2017 | | |
| TW | 200800687 A * | 1/2008 | | A61B 5/145 |
| WO | WO-9422686 A1 * | 10/1994 | | B60K 28/063 |
| WO | WO-2005051700 A1 * | 6/2005 | | B60K 28/063 |
| WO | WO-2007094988 A2 * | 8/2007 | | A61B 5/145 |
| WO | WO-2007095026 A2 * | 8/2007 | | A61B 5/145 |
| WO | WO-2009047074 A1 * | 4/2009 | | B60K 28/063 |
| WO | WO-2009075253 A1 * | 6/2009 | | B60K 28/063 |
| WO | WO-2012039724 A1 * | 3/2012 | | B60K 28/063 |

* cited by examiner

DRUNK DRIVING PREVENTION SYSTEM WITH BYPASS MODE AND DRUNK DRIVING PREVENTION METHOD USING THE SYSTEM

CROSS-REFERENCE TO RELATED APPLICATIONS

The present application claims priority to Korean Patent Application No. 10-2021-0103020, filed Aug. 5, 2021, the entire contents of which is incorporated herein for all purposes by this reference.

TECHNICAL FIELD

The present disclosure relates to a system and method for preventing drunk driving, and more particularly, to a drunk driving prevention technology that allows driving when the drunk driving prevention system malfunctions or in an emergency.

BACKGROUND

Traffic accidents caused by drunk driving lead to major accidents. Ongoing campaign to alert to the gravity of accidents and severity of damages caused by drunk driving is yet to cut down the drunk driving.

Since traffic accidents by drunk driving are very likely to lead to major fatal accidents, measures to stop drunk driving-related accidents are highly needed.

On the other hand, the reality is that the police are running short of officers to run drunk driving crackdowns amid the continued occurrence of drunk driving-related accidents. In addition, since the drunk driving crackdown causes traffic jams, the reality is that frequent drunk driving crackdowns in heavy-traffic areas are not readily welcomed.

Accordingly, attempts are being made to employ a system for preventing drunk driving in a vehicle to stop drunk driving.

In this regard, Korean Patent No. 10-705968 discloses a technology for checking whether a driver is intoxicated using biometric information obtained by bodily contact of the driver with an alcohol detection device and unlocking the shift lever of a vehicle only when the driver is not intoxicated, thereby preventing drunk driving of the vehicle.

In addition, Japanese Unexamined Patent Publication No. 2005-096663 discloses a technology for determining whether a driver is intoxicated using the exhaled breath of the driver and cutting off electricity for the engine start when the driver is determined to be intoxicated, thereby preventing drunk driving.

In addition, Japanese Patent No. 5348457 discloses a driver monitoring apparatus provided with a camera for photographing the driver and an alcohol detection device and provided with an interlocking device blocking engine start when alcohol is detected in the driver's exhaled breath by the alcohol detection device. In particular, Japanese Patent No. 5348457 discloses an apparatus configured to allow engine start only when the identity of the driver is verified based on a plurality of photographs taken by the camera immediately before and after an alcohol detection test by the alcohol detection device.

In contrast, since the conventional drunk driving prevention system only focuses on the function of checking an intoxication state to prevent drunk driving, there is a concern that an emergency, while driving is blocked, may lead to a major accident.

SUMMARY

An object of the present disclosure to address the issue described above is to provide a drunk driving prevention system having a bypass mode and a drunk driving prevention method using the system configured to allow temporary driving of a vehicle in an emergency or when the drunk driving prevention system malfunctions.

In addition, another object of the present disclosure is to provide a bypass control of the drunk driving prevention system that ensures safety by preventing a drunk driving-related accident when the driver performs emergency driving in a bypass mode in an intoxicated state.

According to the present disclosure, the drunk driving prevention system having a bypass mode is a drunk driving prevention system that includes a sensor module measuring the alcohol content in the exhaled breath of a driver at the time of breath-checking of the driver and a control module configured to check the intoxication state of the driver based on the alcohol content measured by the sensor module to determine whether or not the breath-checking is complete and block an engine start when the breath-checking fails, wherein the control module includes a bypass control unit switching a vehicle into a drivable state at the request of the driver when the breath-checking fails.

The control module may further include a malfunction control unit configured to check whether the drunk driving prevention system malfunctions, and the bypass control unit may switch the vehicle into the drivable state even if the breath-checking is not completed when the malfunction of the drunk driving prevention system is detected by the malfunction control unit.

The control module may further include a vehicle state information collection unit collecting and recording in a storage unit the breath-checking information, vehicle information during driving, and driving records, and when driving is allowed at the request of the driver after the breath-checking fails, the vehicle state information collection unit may store in the storage unit one or more information from a group consisting of information on the bypass mode entry time, the face of the driver photographed by the camera, measured alcohol content, departing location, destination, gear shift, vehicle speed, presence of a passenger, and driving locations.

When driving is allowed at the request of the driver after the breath-checking fails, the bypass control unit may send out an alarm through an alarm device to warn neighboring vehicles and pedestrians that the driver is intoxicated.

The bypass control unit may determine the driving allowance time according to the measured alcohol content and output the driving allowance time by a display device of the vehicle.

The bypass control unit may block the engine start to deactivate the bypass mode when the measured alcohol content exceeds bypass reference alcohol content.

The display device may be a navigation device, and the bypass control unit may set a destination through the navigation device when the bypass mode is entered at the request of the driver after the breath-checking fails. When it is determined based on a comparison between the expected driving time to reach the destination and the driving allowance time that the destination may not be reached within the driving allowance time, the bypass control unit may pick out, and guide the vehicle to, a stopover at which the vehicle may stop or park on a driving route to the destination through the navigation device.

In addition, according to the present disclosure, the drunk driving prevention method with a bypass mode includes starting a breath-checking, pulling the exhaled breath of a driver into a sensor module, determining whether the driver is intoxicated by measuring the alcohol content in the exhaled breath of the driver to check the intoxication state of the driver, determining whether or not to block an engine start based on the check result of intoxication, and entering a bypass mode to switch the vehicle into a drivable state at the request of the driver while the engine start is blocked.

Comparing the alcohol content measured by the sensor module with the bypass reference alcohol content after the bypass mode is entered may be further included, and the engine start may be blocked to deactivate the bypass mode when the comparison result shows that the measured alcohol content exceeds the bypass reference alcohol content.

In addition, determining driving allowance time according to the measured alcohol content and outputting the driving allowance time by the display device of the vehicle when the comparison result shows that the measured alcohol content is equal to or less than the bypass reference alcohol content may be further included.

Collecting and storing in a storage unit one or more of the bypass records and driving records by the vehicle state information collection unit may be further included after the driving allowance time is output. The bypass record may include one or more information from a group consisting of the bypass mode entry time, the face of the driver photographed by the camera, and measured alcohol content, and the driving record may include one or more information from a group consisting of the departing location, destination, gear shift, vehicle speed, presence of a passenger, and driving locations.

Transmitting to the server one or more of the bypass records and driving records stored in the storage unit when the preset destination is reached may be further included after the records are stored.

The display device may be a navigation device, and comparing the expected driving time to reach the destination input in the navigation device in advance with the driving allowance time may be further included after the driving allowance time is output. When it is determined based on the comparison result that the destination input in advance may not be reached within the driving allowance time, picking out, and guiding the vehicle to, a stopover at which the vehicle may stop or park on the driving route to the destination by the navigation device may be further included.

When the vehicle is driven by an intoxicated driver after the bypass mode is entered, an alarm may be sent out by an alarm device to warn neighboring vehicles and pedestrians that the driver is intoxicated until the vehicle operation is terminated.

According to the present disclosure, the drunk driving prevention system having a bypass mode and the drunk driving prevention method using the system provides a bypass mode that allows temporary driving of the vehicle while the driver is intoxicated when an emergency arises so that the emergency may be properly coped with.

In particular, according to the present disclosure, temporary driving of the vehicle is allowed when a patient needs emergency medical attention due to childbirth or an injury so that there is an advantage in that a system that allows emergency medical treatment in a nearby hospital even in an emergency may be implemented.

In addition, according to the present disclosure, the driving record is automatically transmitted to the server of the relevant institutes when the vehicle is driven in the bypass mode, thereby blocking abuse of the bypass mode and pre-empting legal disputes in the event of an accident.

In addition, according to the present disclosure, when a vehicle is driven in the bypass mode, the driving distance allowance is variably set according to the intoxication level of the driver and a warning is issued so that neighboring vehicles may be aware of the intoxicated state of the driver, thereby reducing the likelihood of an accident in the bypass mode.

DETAILED DESCRIPTION

A drunk driving prevention system having a bypass mode according to various embodiments of the present disclosure and a drunk driving prevention method using the system will be described with reference to the accompanying drawings in the following.

Figure 1:
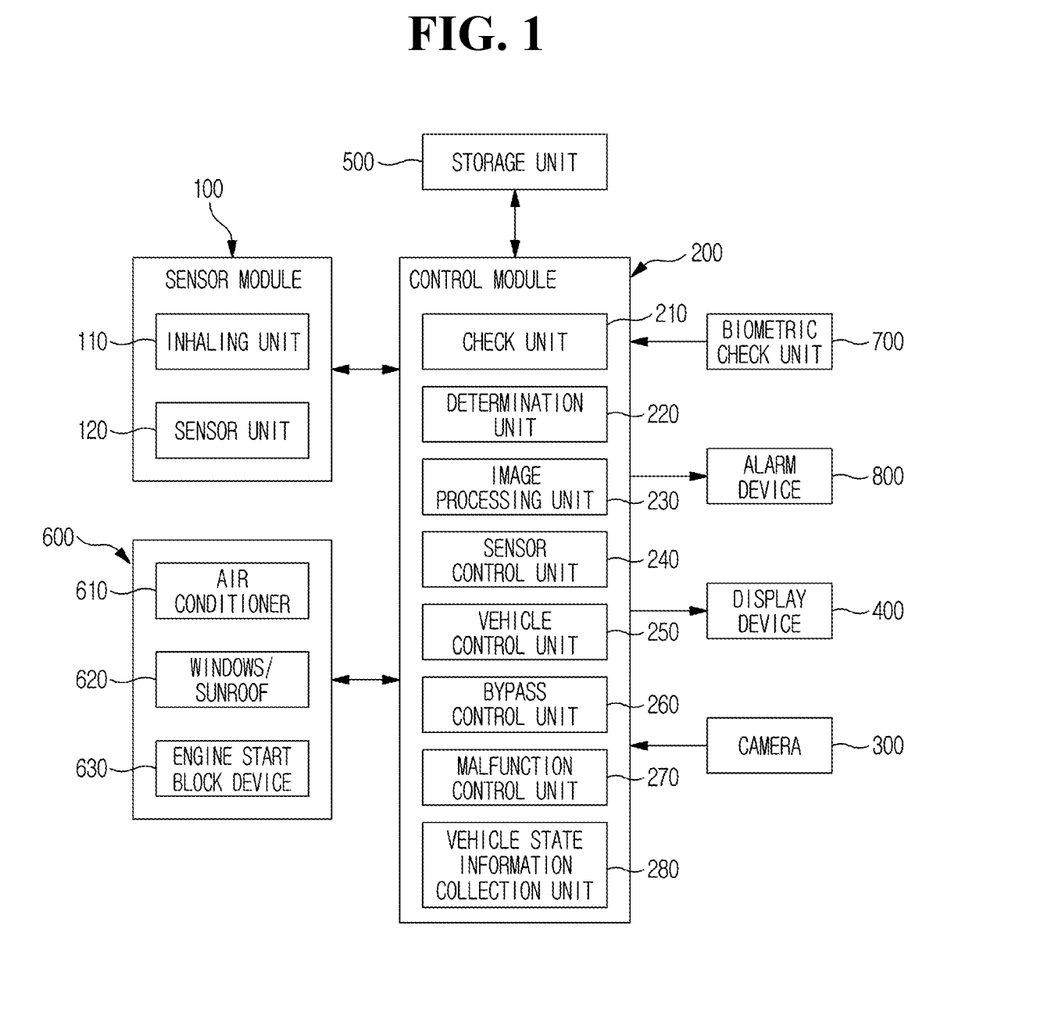
FIG. 1 is a block diagram of a drunk driving prevention system having a bypass mode according to an embodiment of the present disclosure.

FIG. 1 is a block diagram of a drunk driving prevention system having a bypass mode according to an embodiment of the present disclosure.

As illustrated in FIG. 1, according to a preferred embodiment of the present disclosure, the drunk driving prevention system having a bypass mode may include a camera 300 capturing images including the face of a driver seated in a driver's seat, a sensor module 100 measuring the alcohol content in the exhaled breath of the driver, and a control module 200 checking the identity of the driver based on the images captured by the camera 300 and checking the intoxication state of the driver based on the alcohol content measured by the sensor module 100 to activate an engine start block device 630 of the vehicle.

The camera 300 may be installed in the vicinity of the driver's seat inside the vehicle and photograph the driver seated in the driver's seat. The camera 300 may transmit the captured image information to the control module 200 and the control module 200 may perform a subsequent process such as checking the identity of the driver based on the captured images of the driver.

In addition, according to a preferred embodiment of the present disclosure, the drunk driving prevention system may include a storage unit 500 configured to store various information such as image information captured by the camera 300 and alcohol content information measured by the sensor module 100 and a display device 400 configured to display to a driver various information relating to the breath-checking procedure. The display device may be a display device in a vehicle, and preferably may be a navigation device having a display unit such as AVN (audio, video, navigation) device or a cluster.

In particular, according to the preferred embodiment of the present disclosure, the drunk driving prevention system may be a system that includes the control module and the sensor module to implement a bypass mode in a narrow sense or a system that includes configurations such as the camera, the storage unit, and the display device in a broad sense. However, configurations such as the camera and the storage unit are not ruled out even in the system in a narrow sense and the system may be implemented by interlocking the camera, the storage unit, and the display unit provided in the vehicle system with the control module and the sensor module.

According to a preferred embodiment of the present disclosure, the sensor module 100 may include an inhaling unit 110 pulling exhaled breath of a driver and a sensor unit 120 provided with an alcohol content measurement sensor measuring the alcohol content in the exhaled breath of the driver.

The inhaling unit 110 may be installed at a position where the breath exhaled by the driver may be easily pulled, and may preferably be installed in the vicinity of the cluster, steering wheel, or center fascia.

In particular, the inhaling unit 110 of the sensor module 100 is provided with a fan driven by a motor, and the air intake may be increased or decreased by controlling the rotation speed of the fan. The fan is installed in the inlet portion of the inhaling unit 110, and the motor for driving the fan may be controlled by a control unit of the sensor module 100 or a sensor control unit 240 of the control module 200.

In addition, the sensor unit 120 detects alcohol content in the air pulled into the inhaling unit 110 and preferably measures the alcohol content in the breath exhaled by the driver toward the sensor module 100. Information on the detected alcohol, more preferably the measured alcohol content in the exhaled breath, may be transmitted to the control module 200. Accordingly, the control module 200 may compare the measured alcohol content with the preset reference alcohol content and determine whether the driver is intoxicated and whether the driver is allowed to drive.

According to the preferred embodiment of the present disclosure, the drunk driving prevention system may include a display device for displaying various information. The display device 400 may be a display in the instrument cluster of the vehicle or may be provided separately.

The display device 400 may display various information that the driver needs to be informed of in the process of operating the drunk driving prevention system. In particular, the guide information on the breath-checking procedure and bypass mode entry may be displayed.

For example, the display device 400 may display a message on the open/closed state of all windows, an instruction to close the windows, and the like. Once the breath-checking starts, messages relating to the specific information on whether the breath-checking is complete, an instruction to repeat the breath-checking, a cause of breath-checking failure, and the like may be displayed. In addition, when the bypass mode is entered at the request of the driver, related guide information may be displayed on the display device.

According to the present disclosure, the drunk driving prevention system may include a storage unit 500. Various information including the image information captured by the camera 300 in the process of breath-checking, alcohol content measurement information as measured by the sensor module 100, and the like may be stored in the storage unit 500. The image information may include the time of image capture, the driver's face, and the like.

In addition, when the vehicle is driven in the bypass mode, the driving records, for example, the departing location, destination, gear shift, speed, presence of a passenger, driving route, and the like may be stored in the storage unit 500. The vehicle information relating to the driving records in the bypass mode may be stored and managed as the bypass mode records together with the captured image information and alcohol detection information recorded at the time of the breath-checking and may be transmitted to the server by the in-vehicle communication module.

In addition, the storage unit 500 may store vehicle information including the open/closed state of windows and the operating state of an air conditioner before the breath-checking starts. In checking the intoxication state of the driver, the breath-checking is preferably performed in the inside air mode with all windows/sunroof 620 closed for accurate measurement so that the control module 200 closes the windows/sunroof 620 and switches the vehicle into the inside air mode once the breath-checking starts. To this end, a vehicle control unit 280 of the control module 200 may transmit a control command to open/close the windows/sunroof 620 or switch between the inside and outside air modes of an air conditioner. In addition, the vehicle control unit 280 may close the vehicle doors for the breath-checking.

At this time, the information stored in advance before the breath-checking refers to the information on the surrounding environment set by the driver before checking the intoxication state. Accordingly, after the breath-checking is completed, the control module 200 switches the vehicle state according to the vehicle information stored in the storage unit 500 before the breath-checking so that the in-vehicle device 600 may return to the previous states set by the driver. However, since opening the vehicle door is not possible, the door state is preferably not stored in the storage unit 500.

According to the preferred embodiment of the present disclosure, the drunk driving prevention system may further include a biometric check unit 700 for checking the identity of the driver. The biometric check unit 700 checks the driver information and may include a biometric identification device configured to check the fingerprint or iris information of the driver.

The storage unit 500 may store the biometric information of a specific driver in advance, and the check unit 210 may compare the stored biometric information with the biometric information of the current driver obtained through the biometric check unit 700 to perform the identity check process.

In addition, the control module 200 may be connected to other configurations in the system such as the sensor module 100, camera 300, display device 400, and storage unit 500 through a communication interface and control the entire system according to the information transmitted from these configurations.

The control module 200 may include a check unit 210, a determination unit 220, an image processing unit 230, a sensor control unit 240, a vehicle control unit 250, a bypass control unit 260, a malfunction control unit 270, and a vehicle state information collection unit 280. The respective configurations included in the control module 200 are classified according to functions performed by the control module 200 and the respective configurations constituting the control module 200 are not necessarily separated physically. Configurations other than the bypass control unit 260, the malfunction control unit 270, and the vehicle state information collection unit 280, that is, the check unit 210, the determination unit 220, the image processing unit 230, the sensor control unit 240, and the vehicle control unit 250 are configurations provided as illustrative examples to describe the general functions of the drunk driving prevention system. Any configuration that may implement a drunk driving prevention system even when some of these configurations are missing may be employed in the control module of the present disclosure. In addition, the respective configurations in the control module may communicate with each other.

According to the preferred embodiment of the present disclosure, the control module 200 is a controller configured to perform various functions such as breath-checking, intoxication state determination, and vehicle control and may include a processor executing calculations and a memory in which an algorithm to perform functions of the processor is stored to perform these functions. In addition, the control module 200 may be modularly provided with the check unit 210, the determination unit 220, the sensor control unit 240, the vehicle control unit 250, the bypass control unit 260, the malfunction control unit 270, and the vehicle state information collection unit 280. In addition, the sub-configurations of the control module 200 are illustrative examples. The control module 200 may perform the same or equivalent functions while communicating with other vehicle controllers, in which case some sub-configurations may be removed or replaced.

Among the basic configurations of the control module, the check unit 210 may oversee the breath-checking process, and the determination unit 220 may compare the alcohol content measured by the sensor module 100 with the reference alcohol content to check the intoxication state of the driver.

The check unit may check whether the driver is seated from the information provided by devices such as a weight sensor of the driver's seat or a camera 300 photographing the driver's seat and check the identity of the driver from the images captured by the camera 300. In addition, the check unit 120 may determine whether the breath-checking is complete based on the breath amount of the driver provided to the sensor module 100.

Here, the breath-checking refers to a process in which the breath of the driver is pulled, the alcohol content in the exhaled breath of the driver is measured by the sensor module 100, and whether the driver is intoxicated is determined according to the alcohol content measured by the sensor module. In addition, that the breath-checking is complete means that the procedure in which the control module determines that the alcohol content in the exhaled breath of the driver is within a reference value and that the driver is fit for driving is completed.

For example, once the breath-checking starts by the check unit 210, the sensor module 100 measures the alcohol content in the exhaled breath of the driver, the information on the measured alcohol content is transmitted to the control module 200, and the determination unit 220 of the control module 200 compares the alcohol content measured by the sensor module 100 with the reference alcohol content to check the intoxication state of the driver.

When the comparison result shows that the alcohol content exceeds the reference alcohol content and the driver is determined to be intoxicated, the determination unit 220 may determine that the driver may not drive (breath-checking failure) due to intoxication, and the vehicle control unit 250 of the control module 200 may activate an engine start block device 630. In this regard, the engine start block device 630 refers to a device that blocks the engine start to disable the vehicle. For example, the engine start block device may be a device that cuts off ignition power. In contrast, when the measured alcohol content of the driver is within the reference alcohol content, it may be determined that the driver is fit for driving and that the breath-checking is completed.

The image processing unit 230 processes the image information captured by and received from the camera 300 into the image information necessary for the control module 200. The sensor control unit 240 controls the sensor module and may control the rotation speed of the fan of the sensor module 100, the sensitivity of the sensor module 100, and the like. The vehicle control unit 250 may transmit control commands to other in-vehicle devices 600 such as vehicle doors, windows/sunroof 620, an air conditioner 610, an engine start block device 630, and the like.

The bypass control unit 260 may switch the vehicle into a drivable state in the bypass mode by bypassing the drunk driving prevention system when an emergency occurs or when the drunk driving prevention system malfunctions. The bypass control unit 260 may implement the bypass mode at the request of the driver in an emergency.

When the bypass mode is executed at the request of the driver, the vehicle is switched into a drivable state even without going through the breath-checking logic. Accordingly, even when the driver may not execute the breath-checking (system malfunction) or the breath-checking fails, the vehicle system may be controlled in the bypass mode so that the engine start block device is deactivated such that the locks on the engine start, steering wheel, gear shift, acceleration pedal, and the like are lifted.

However, when the alcohol content measured by the sensor module exceeds the bypass reference alcohol content, the bypass control unit 260 may disallow entry into the bypass mode. The bypass reference alcohol content may be the alcohol content corresponding to a highly intoxicated state that precludes driving even in an emergency. Accordingly, the bypass reference alcohol content is greater than the reference alcohol content for passing the breath-checking. Accordingly, when the alcohol content measured by the sensor module exceeds the bypass reference alcohol content, the driver may not drive so that the bypass mode may be deactivated. Accordingly, when the measured alcohol content exceeds the bypass reference alcohol content, the engine start may be blocked by the engine start block device.

The malfunction control unit 270 may check the malfunction of the drunk driving prevention system and transmit an error code relating to the malfunction. According to the present disclosure, the malfunction control unit 270 of the drunk driving prevention system may perform a self-check and execute a self-repair processing of the system to resolve a system abnormality. However, when the malfunction issue is not resolved despite the self-repair processing, the malfunction control unit transmits an error code.

When the malfunction control unit transmits the error code, the bypass control unit 260 detects the malfunction and may switch the vehicle into the bypass mode. Accordingly, when the drunk driving prevention system malfunctions, the driver may be provided with a bypass route to drive the vehicle in the bypass mode without going through the breath-checking.

The vehicle state information collection unit 280 may collect the vehicle state information such as the breath-checking information in the breath-checking procedure, vehicle information and driving records during vehicle operation, and the like. The vehicle state information collection unit 280 may be connected to other in-vehicle devices through a communication interface and receive information from configurations that detect or store respective vehicle state information.

In particular, when the bypass function is activated, the vehicle state information collection unit 280 may collect and transmit to the storage unit the breath-checking information and vehicle operation information in the bypass mode so that the information is recorded in the storage unit.

For example, when the vehicle is driven in the bypass mode, the vehicle state information collection unit 280 may collect the time of the bypass mode driving, face of the driver, alcohol content of the driver, departing location, destination, and various vehicle information during operation such as gear shift, vehicle speed, presence of a passenger, driving location information, and the like. Of the information collected by the vehicle state information collection unit 280, for the convenience of description, the major information at the time of bypass mode entry, the face of the driver, the alcohol content of the driver, and the like will be referred to as a bypass record while various vehicle information during driving such as the departing location, destination, various vehicle information during driving, and the like will be referred to as a driving record.

The vehicle state information collection unit 280 may transmit to and record in the storage unit the collected information in real-time. For example, when the bypass mode is entered before the vehicle is driven, the bypass record may be stored in the storage unit, and the vehicle state information collected in real-time while the vehicle is driven may be stored in the storage unit as the driving record.

The bypass record and driving record stored in the storage unit may be transmitted to the server through an in-vehicle communication module after the destination is reached and the vehicle operation is terminated. In this regard, the server may be a server of relevant institutes such as the police depart or a business owner.

In this regard, the input of the destination through an in-vehicle navigation device is preferably made mandatory when the bypass mode is entered. If the destination is initially input, the bypass record and driving record may be transmitted to the server immediately after the destination is reached.

As described above, the mandatory input of the bypass record and driving record in the storage unit when the bypass mode is entered and the subsequent transmission of the records to a specific server by the vehicle state information collection unit 280 may prevent drivers from abusing the bypass mode and reduce the likelihood of accidents.

In addition, according to the preferred embodiment of the present disclosure, the drunk driving prevention system may warn the neighboring vehicles and pedestrians that the vehicle is driven in the bypass mode by the bypass control unit 260. For example, when an intoxicated driver operates a vehicle, the bypass control unit 260 sends out an alarm an alarm device 800 to warn neighboring vehicles and pedestrians that an intoxicated driver drives the vehicle in the bypass mode until the vehicle operation is terminated. The alarm device 800 may be a lamp or a sound generator, and the alarm by the alarm device 800 may be lighting a lamp or sounding a warning. In the example, drivers of nearby vehicles may check the light lamp or warning sound of the vehicle to learn that the vehicle is driven by an intoxicated driver and drive defensively to avoid an accident.

In addition, the alarm device 800 may be an external display device, and the external display device may warn neighboring vehicles and pedestrians that an intoxicated driver drives the vehicle in the bypass mode by a visual display such as a text.

Also, when V2X (Vehicle to Everything) is available such that information may be shared between vehicles, the information that the vehicle is driven in the bypass mode may be transmitted vehicle to vehicle (V2V).

However, since sending out an alarm that the vehicle is driven in the bypass mode to the neighboring vehicles and pedestrians is preferably limited to the drunk driving case, the alarm device preferably does not send out an alarm to the neighboring vehicles and pedestrians when the entry into the bypass mode is due to a system malfunction.

On the other hand, according to the preferred embodiment of the present disclosure, the bypass control unit 260 may set different driving allowance times according to the measured alcohol content of the driver.

Since the driving allowance time is the time the driver is allowed to drive in the bypass mode without going through the breath-checking, the driving allowance time may be immediately determined according to the measured alcohol content when the bypass mode is entered. In addition, the driving allowance time may be converted into a distance conceptually, and the driving distance allowance may be set in another embodiment.

The driving allowance time may be variably set by the bypass control unit 260. For example, the driving allowance time may be variably set according to the alcohol content information of the driver measured by the sensor module. In the present disclosure, the driving allowance time is set in reflection of the intoxicated state of the driver, that is, the magnitude of the alcohol content of the driver above the reference value, and from the view of driving safety, the driving allowance time is preferably set short when the alcohol content is high and that the driving allowance time is set long when the alcohol content is low. For example, the driving allowance time may be set to linearly decrease as the alcohol content increases. The driving allowance time according to the alcohol content may be preset by the mapped data, and the bypass control unit 260 determines the driving allowance time according to the measured alcohol content value based on the mapped data.

The driving allowance time is a limit to the time the driver is allowed to drive in the bypass mode. The display device may display the driving allowance time to the driver when the bypass mode is entered. In addition, the display device may display the remaining driving allowance time while the vehicle is driven in the bypass mode.

On the other hand, when the driving time in the bypass mode exceeds the driving allowance time, the driver may be alerted to the excess through a message by the display device. The driver may preferably be alerted to the approaching expiration of the driving allowance time before the driving allowance time expires. For example, the remaining driving allowance time may be sequentially displayed according to predetermined criteria like 5 minutes, 2 minutes, 1 minute, and 30 seconds before the expiration of the driving allowance time.

Accordingly, the sequential display of the remaining driving allowance time enables the driver to check the remaining time and leads the driver to stop or park the vehicle at an appropriate place when the destination may not be reached within the remaining time. In this regard, technology for predicting an expected time of arrival at the destination or the required time to reach the destination in the conventional navigation device may be employed in determining whether the destination may be reached within the remaining time. The possibility of reaching the destination may be determined by comparing the time predicted through the technology with the remaining time.

More preferably, the bypass control unit 260 may pick out, and guide the vehicle to, a place where the vehicle may stop or park within the driving allowance time through the navigation device. In this case, the stopover may be a place having a space for temporary parking on the road such as a gas station, a drowsiness shelter, a rest area, or a large restaurant. Accordingly, according to a preferred embodiment of the present disclosure, when it is determined that the vehicle may not reach the destination within the remaining driving allowance time, the bypass control unit 260 may automatically pick out a stopover and issue a message instructing the driver to temporarily park the vehicle at the picked stopover through the navigation device. At this time, the stopover in the shortest distance may be picked out from among potential candidate places.

In addition, the engine is preferably not turned off immediately for safety even when the driving allowance time expires and that the engine is turned off when the vehicle moves to a safe place and stops or parks.

When the vehicle is driven longer than the driving allowance time, the bypass control unit 260 may alert the driver to the expiration of the driving allowance time through the display device and transmit the expiration information to the server through the communication module.

After the driving allowance time expires, the driver may resume driving after going through another breath-checking process. In this case, if the alcohol content turns out to be equal to or less than the reference alcohol content, driving may be resumed immediately. In contrast, if the alcohol content still exceeds the reference alcohol content, driving may be resumed only in the bypass mode, and bypass control may be performed in the same manner as before.

On the other hand, the driving allowance time may not apply even when the vehicle is driven in the bypass mode if the drunk driving prevention system malfunctions.

A drunk driving prevention method using the drunk driving prevention system that has the bypass mode with the configurations described above will be described with reference to FIGS. 2 and 3.

Figure 2:
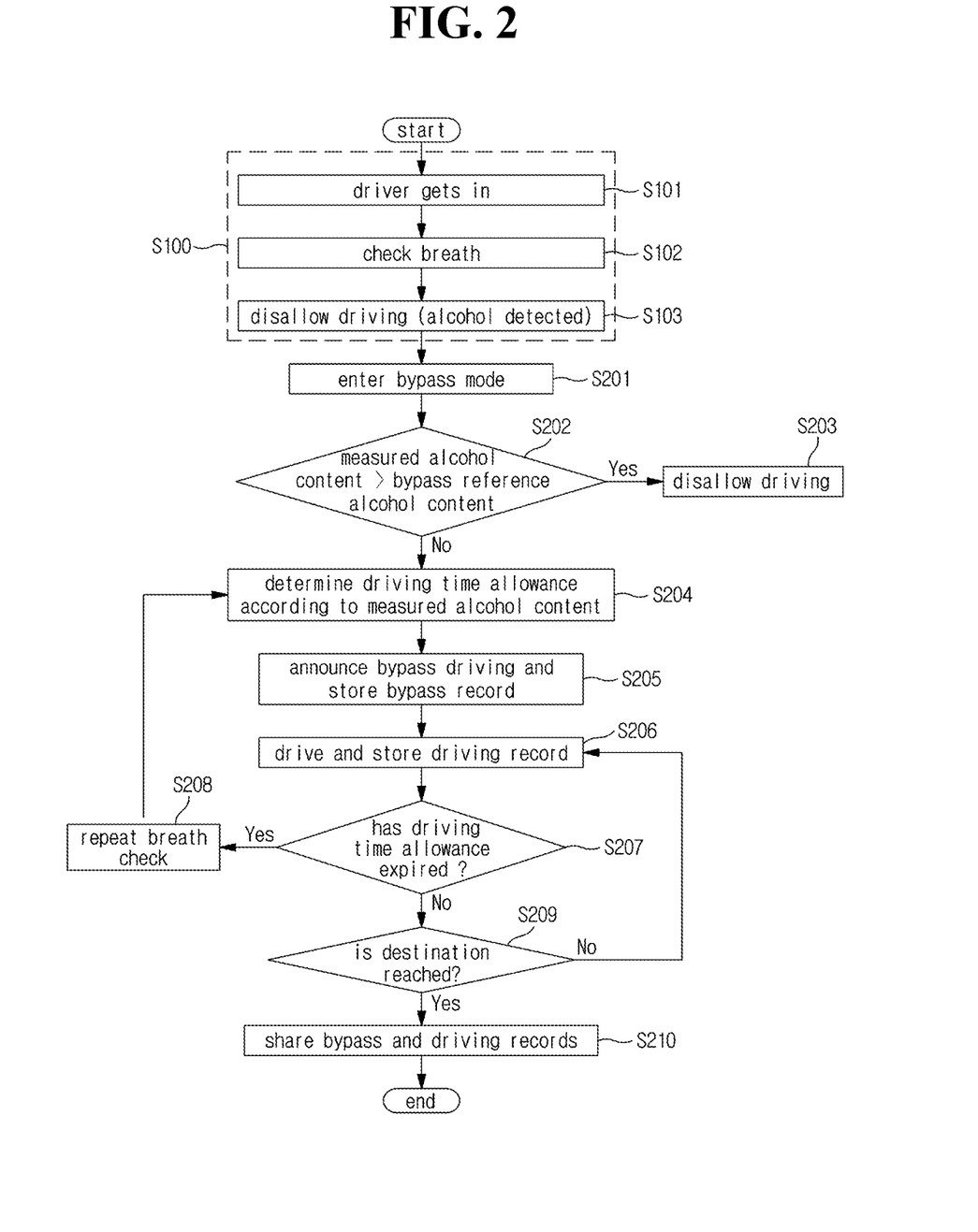
FIG. 2 is a flowchart of a drunk driving prevention method having a bypass mode according to an embodiment of the present disclosure.
Figure 3:
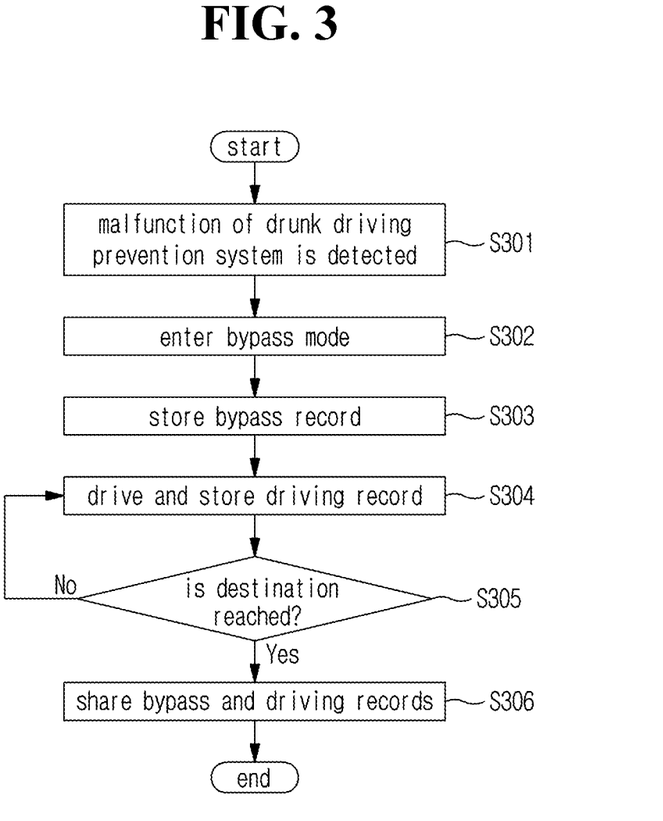
FIG. 3 is a flowchart for describing a bypass mode when a drunk driving prevention system malfunctions according to an embodiment of the present disclosure.

FIG. 2 is a flowchart of a drunk driving prevention method having a bypass mode according to an embodiment of the present disclosure, and FIG. 3 is a flowchart for describing a bypass mode when the drunk driving prevention system malfunctions according to an embodiment of the present disclosure.

According to the present disclosure, the drunk driving prevention method having a bypass mode includes starting a breath-checking, pulling the exhaled breath of a driver into a sensor module, determining whether the driver is intoxicated by measuring the alcohol content in the exhaled breath of the driver, and determining whether or not to block engine start based on the check result of intoxication.

By the method described above, the exhaled breath of the driver is pulled into the sensor module, the alcohol content in the exhaled breath of the driver is measured by the sensor module, the measured alcohol content is compared with a preset reference alcohol content, and the intoxication state of the driver relating to whether the driver is allowed to drive may be checked. However, the steps are illustrative examples only. Any method of measuring the alcohol content by a driver's breath-checking process and determining whether or not to allow driving based on the analysis result may be equally employed.

FIG. 2 shows that the process of determining whether or not to allow an intoxicated driver to drive may be summarized in step S100 indicated by a dotted line and includes preliminary steps before the bypass mode is entered. In the example in FIG. 2, a driver gets in a vehicle (S101), a breath of the driver is checked (S102), and whether or not to allow the driving is determined based on the check result. Accordingly to a preferred embodiment of the present disclosure, when the comparison result shows that the driver may not drive, that is, the measured alcohol content in the exhaled breath of the driver exceeds a reference value, the driver is disallowed from driving in a normal step. Accordingly, step S103 presupposes that driving is disallowed due to the intoxication of the driver.

On the other hand, the preferred embodiment of the present disclosure provides the bypass mode activated at the request of the driver when there is an urgent need to move in a vehicle due to childbirth or an injury.

The specific steps relating to the bypass mode are described in step S201 and below.

When it is determined that driving is disallowed in the previous step S100, the engine start block device is activated to block the engine start.

When a request by a driver to enter the bypass mode is entered into the system while the engine start is blocked, a step S201 of entering the bypass mode is executed.

When the bypass mode is entered, the engine start block is lifted to switch the vehicle into a state in which the engine start is allowed. However, even when the engine start block is lifted, the vehicle may not be driven immediately. For example, even when the vehicle engine is turned on, the gear shift may remain in P gear with no further shift so that the vehicle may not be instantly driven. Also, manipulation of the steering wheel in addition to the gear shift may still be blocked.

In contrast, according to the preferred embodiment of the present disclosure, when the driving allowance time to be described below is set, driving in the bypass mode is finally allowed so that locks on the gear shift and the steering wheel may be lifted to allow driving after the driving allowance time is set.

Comparing the alcohol content measured by the sensor module with the bypass reference alcohol content (S202) may be performed after the bypass mode is entered (S201). When the measured alcohol content exceeds the bypass reference alcohol content, it may be determined that driving is not allowed (S203) and the engine start may be blocked to deactivate the bypass mode.

In addition, when the comparison result shows that the measured alcohol content is equal to or less than the bypass reference alcohol content, the driving allowance time is determined according to the measured alcohol content and the display device of the vehicle may output the driving allowance time (S204).

When the driving allowance time in the bypass mode is set in the system, that the vehicle is driven in the bypass mode may be announced and the bypass record may be stored in the storage unit (S205).

Announcing the driving in the bypass mode is announcing that the vehicle is driven in the bypass mode inside and outside the vehicle. For example, the in-vehicle display device may display to the driver the start of driving in the bypass mode. Also, the alarm device 800 may send out an alarm that neighboring vehicles or pedestrians may recognize. For example, the alarm device 800 may send out an alarm to warn neighboring vehicles and pedestrians that the driver is intoxicated, and the alarm may continue until the vehicle operation is terminated.

In addition, the bypass record in step S205 may include one or more from a group consisting of the bypass mode entry time, face of the driver photographed by the camera, and measured alcohol content collected by the vehicle state information collection unit 280.

When the vehicle is driven in the bypass mode, the driving records collected by the vehicle state information collection unit 280 may be stored in the storage unit (S206). The driving records may include one or more information from a group consisting of the departing location, destination, gear shift, vehicle speed, presence of a passenger, and driving locations. The driving records are stored in real-time while the vehicle is driven.

On the other hand, the bypass control unit 260 checks whether the preset driving allowance time has expired while the vehicle is driven in the bypass mode (S207). At this time, the remaining driving allowance time may be sequentially displayed according to the preset remaining time allowance before the driving allowance time expires.

When the driving allowance time expires before the destination is reached and the vehicle operation in the bypass mode is terminated, the breath-checking is repeated (S208). The repeated breath-checking process is a process in which the driver exhales a breath into the sensor module and the alcohol content is measured, as in the previous step S102.

In contrast, in determining whether the destination is reached (S209), when the destination is reached before the driving allowance time expires and driving in the bypass mode is terminated, the bypass records and driving records are transmitted to the server of, and shared with, the specific institutes (S210).

In addition, according to the preferred embodiment of the present disclosure, when the bypass mode is entered, the navigation device may instruct the driver to input the destination, and the input destination may be used in determining whether the destination may be reached within the driving allowance time. For example, the bypass control unit 260 may compare the expected time of arrival at the destination input into the navigation device in advance with the driving allowance time and determine whether the input destination may be reached within the driving allowance time.

When the comparison result shows that the destination may not be reached within the driving allowance time, the navigation device may pick out, and guide the vehicle to, a stopover at which the vehicle may stop or park on the driving route to the destination. In this regard, the previous destination information may be deleted and the stopover may be set as a new destination.

FIG. 3 is a flowchart of a drunk driving prevention method having the bypass mode according to the preferred embodiment of the present disclosure. The method is to resolve the issue of engine start block when the drunk driving prevention system malfunctions.

Accordingly, the logic for controlling a series of steps in FIG. 3 may be stored and executed in the drunk driving prevention system and preferably be stored in the system together with the bypass control logic when the breath-checking fails in FIG. 2. The process in FIG. 3 is executed when the system malfunctions.

FIG. 3 shows that the malfunction control unit 270 transmits an error code when a malfunction of the drunk driving prevention system is detected (S301), and the vehicle enters the bypass mode by the bypass control unit 260 that receives the transmitted error code (S302). When the bypass mode is entered due to a system malfunction, the breath of the driver may not be checked and the vehicle may be started without the breath-checking.

Thereafter, once the bypass mode is entered, the bypass record including the malfunction error code is stored in the storage unit (S303), and once the vehicle starts to be driven, the driving record is also stored in the storage unit (S304). When a system malfunction, not an intoxicated state of the driver, leads to an entry into the bypass mode, the driving distance allowance is preferably free of a limit in consideration of the convenience of the driver, unlike the case in FIG. 2.

When the destination is reached and vehicle operation is terminated (S305), the bypass record and driving record are transmitted to the server of, and shared with, specific institutes (S306).

As described above, the drunk driving prevention system and method having the bypass mode allow driving in the way of bypassing the drunk driving prevention system when an emergency occurs or the system malfunctions. In addition, various safety factors such as bypass reference alcohol content, driving distance allowance, and automatic record sharing method are employed to minimize the risk of an accident in implementing the drunk driving prevention system and method having the bypass mode such that it is confirmed that the applicability of the system is greatly enhanced.

A specific embodiment of the present disclosure is illustrated and described, but it will be obvious to those skilled in the art that the present disclosure may be improved upon and modified in various manners without deviating from the technical spirit of the present disclosure provided in the following claims.

What is claimed is:

1. A system for bypassing a drunk driving prevention function of a vehicle, comprising:
   a sensor module configured to measure, during breath-checking a driver of a vehicle, alcohol content in the driver's exhaled breath; and
   a control module configured to (1) check, during the breath-checking of the driver, whether the driver is intoxicated based on the alcohol content measured by the sensor module, (2) determine whether or not the breath-checking of the driver is completed based on whether checking the driver is intoxicated has been completed, and (3) block starting of an engine of the vehicle when the driver fails the breath-checking,
   wherein the control module includes a bypass control unit configured to (1) receive, from the driver, a request to allow the driver to drive the vehicle after the driver fails the breath-checking, and (2) in response to receiving the request from the driver, causing the vehicle to enter a bypass mode in which the driver is allowed to drive the vehicle, and
   wherein the bypass control unit is further configured to (1) compare the measured alcohol content with bypass reference alcohol content after the vehicle enters the bypass mode, and (2) deactivate the bypass mode when the measured alcohol content exceeds the bypass reference alcohol content.

2. The system of claim 1, wherein:
   the control module further includes a malfunction control unit configured to determine whether the system malfunctions, and
   the bypass control unit is configured to cause the vehicle to enter the bypass mode before the breath-checking is not completed when the malfunction control unit determines that the system is malfunctioning.

3. The system of claim 1, wherein:
   the control module further includes a vehicle state information collection unit configured to collect and record, in a storage unit, at least one of breath-checking information, vehicle driving information, and vehicle driving records, and when the driver is allowed to drive the vehicle based on the request from the driver after the driver fails the breath-checking, the vehicle state information collection unit is configured to store, in the storage unit, at least one of a bypass mode entry time, an image capturing the driver's face, the driver's measured alcohol content, departing location information, destination information, gear shift information, vehicle speed information, passenger presence information and driving location information.

4. The system of claim 1, wherein, when the driver is allowed to drive the vehicle based on the request from the driver after the driver fails the breath-checking, the bypass control unit is configured to cause an alarm device of the vehicle to output a warning that the driver is intoxicated.

5. The system of claim 1, wherein the bypass control unit is configured to determine a driving allowance time based on the measured alcohol content of the driver, and output, via a display of the vehicle, the driving allowance time.

6. The system of claim 5, wherein:
the display comprises a navigation device, and
the bypass control unit is configured to:
    set a destination through the navigation device when the vehicle has entered the bypass mode based on the request from the driver after the driver fails the breath-checking, and
    select and guide the vehicle to a stopover on a driving route to the destination when it is determined that the destination cannot be reached within the driving allowance time.

7. A method of bypassing a drunk driving prevention function of a vehicle, comprising:
breath-checking a driver of the vehicle to measure alcohol content in the driver's exhaled breath;
determining, based on the measured alcohol content, whether the driver is intoxicated;
in response to determining that the driver is intoxicated, blocking starting of an engine of the vehicle;
after blocking the starting of the engine, receiving, from the driver, a request to allow to drive the vehicle;
in response to receiving the request from the driver, causing the vehicle to enter a bypass mode in which the driver is allowed to drive the vehicle;
comparing the measured alcohol content with bypass reference alcohol content after the vehicle enters the bypass mode; and
deactivating the bypass mode in response to the measured alcohol content exceeds the bypass reference alcohol content.

8. The method of claim 7, further comprising:
determining a driving allowance time based on the measured alcohol content; and
outputting, via a display of a vehicle, the driving allowance time when the measured alcohol content is equal to or less than the bypass reference alcohol content.

9. The method of claim 8, further comprising collecting and storing, in a storage unit, bypass record or driving record after the driving allowance time is determined,
wherein the bypass record includes at least one of a bypass mode entry time, an image capturing the driver's face and the measured alcohol content, and
wherein the driving record includes at least one of departing location information, destination information, gear shift information, vehicle speed information, passenger presence information and driving location information.

10. The method of claim 9, further comprising transmitting, to a server, the bypass record or driving record when the vehicle reaches a destination.

11. The method of claim 8, further comprising:
comparing an expected driving time for the vehicle to reach a destination with the driving allowance time; and
selecting and guiding the vehicle to a stopover on a driving route to the destination when it is determined that the vehicle cannot reach the destination within the driving allowance time.

12. The method of claim 7, further comprising, in response to determining that the driver is intoxicated after the vehicle enters the bypass mode, controlling an alarm device of the vehicle to output a warning that the driver is intoxicated.

* * * * *